United States Patent
Betbeder et al.

(12) 
(10) Patent No.: US 6,214,621 B1
(45) Date of Patent: Apr. 10, 2001

(54) CONJUGATES OF A PARTICLE VECTOR AND OLIGONUCLEOTIDES, PROCESS FOR THEIR PREPARATION, AND PHARMACEUTICAL COMPOSITIONS CONTAINING THEM

(75) Inventors: Didier Betbeder, Aucamville; Roger Kravtzoff, Fourquevaux; Ignacio de Miguel, Plaisance du Touch; Sophie Sixou, Toulouse, all of (FR); Pamela Pavco, Lafayette; Thale Jarvis, Boulder, both of CO (US)

(73) Assignee: Biovector Therapeutics, S.A., Labege Cedex (FR)

( * ) Notice: Subject to any disclaimer, the term of this patent is extended or adjusted under 35 U.S.C. 154(b) by 0 days.

(21) Appl. No.: 09/331,912
(22) PCT Filed: Dec. 27, 1997
(86) PCT No.: PCT/FR97/02332
   § 371 Date: Sep. 30, 1999
   § 102(e) Date: Sep. 30, 1999
(87) PCT Pub. No.: WO98/29557
   PCT Pub. Date: Jul. 9, 1998

(30) Foreign Application Priority Data

Dec. 27, 1996 (FR) .................................................. 96 16121

(51) Int. Cl.$^7$ ................. C12P 7/18; C12Q 1/68; C07H 21/02; C07H 21/04; A61K 51/00
(52) U.S. Cl. .............. 435/458; 435/6; 435/91.1; 435/91.31; 435/320.1; 435/375; 435/459; 536/23.1; 536/24.5; 424/1.29; 424/461; 424/9.35; 424/452; 424/458; 424/1.21
(58) Field of Search ................... 424/1.21, 1.29, 424/1.73, 450; 514/44, 2; 530/402; 435/6, 91.1, 91.31, 91.5, 91.51, 325, 455, 458, 459, 465, 179, 366, 375, 320.1; 536/1.11, 23.1, 24.5, 25.3; 935/33, 34, 36, 54

(56) References Cited

FOREIGN PATENT DOCUMENTS

92/21329 * 12/1992 (WO) ............................... A61K/9/50
92/21330 * 12/1992 (WO) ............................... A61K/9/50

OTHER PUBLICATIONS

Peyrot, M. et al. 1994 International Journal of Pharmaceutics. vol. 102, pp. 25–33.*
De Miguel et al. 1995 Biochim et Biophys. Acta vol. 1237, pp. 49–58.*
Berton, M. et al. 1997. Biochim et Biophys Acta. vol. 1355, pp. 7–19.*
Branch, A. 1998 Trends in Bioch. Sci (TIBS) vol. 23 : pp. 45–50.*
Crooke, St. 1998 Antisense Research & Applica., Chapter 1, pp. 1–50. Springer–Verlag—Publishers.*

* cited by examiner

Primary Examiner—Remy Yucel
Assistant Examiner—Jane Zara
(74) Attorney, Agent, or Firm—Hoffmann & Baron, LLP; Irving N. Feit

(57) ABSTRACT

The invention relates to an ionic conjugate, which is stable in a biological medium, and which is comprised of a particle vector with at least one cationic, nonliquid, hydrophilic nucleus and of polyanionic oligonucleotides. The invention further concerns the pharmaceutical compositions containing these conjugates and the use of a particle vector to carry the oligonucleotides to the cells.

30 Claims, 10 Drawing Sheets

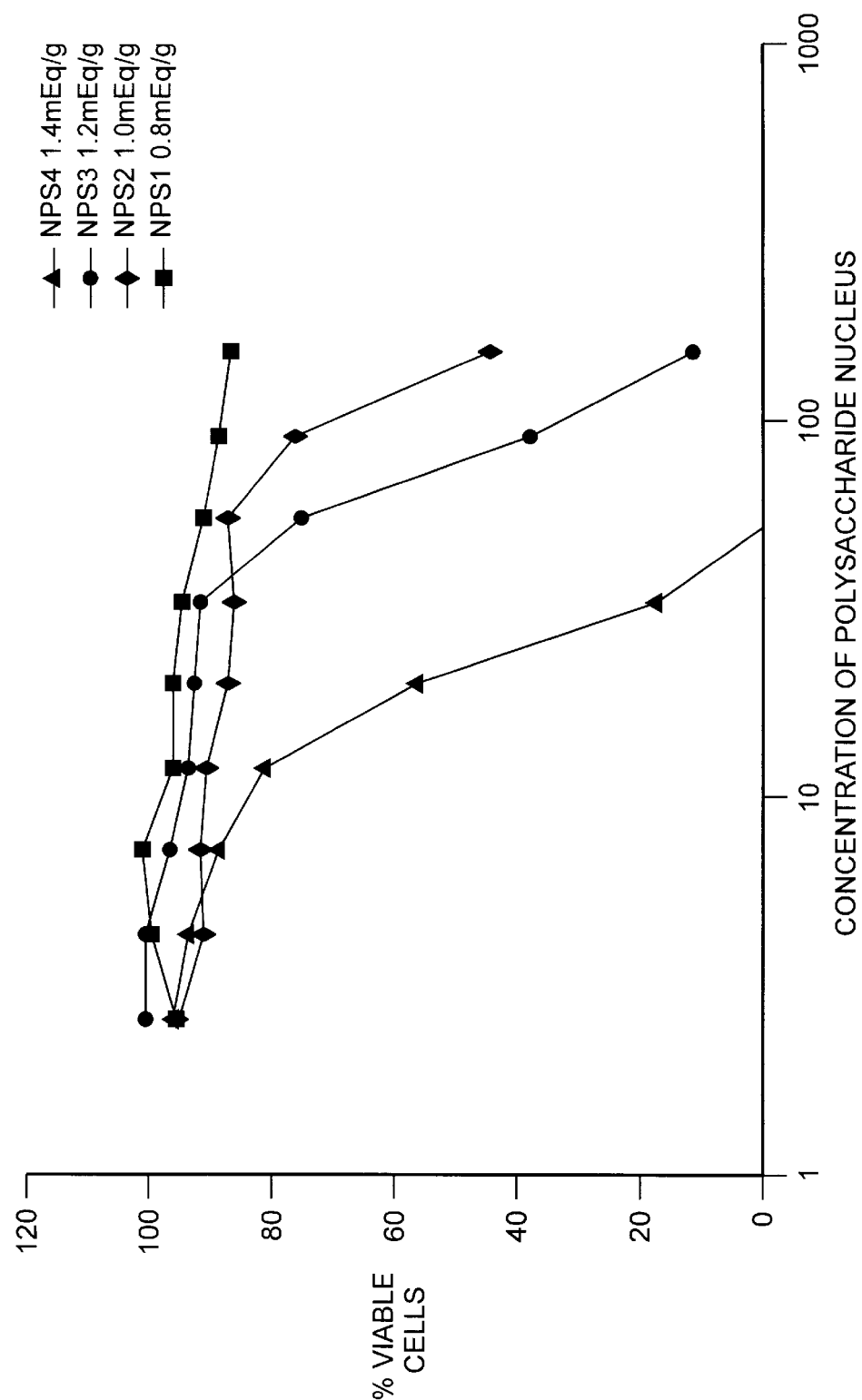
FIG. 1 EFFECT OF THE IONIC CHARGE

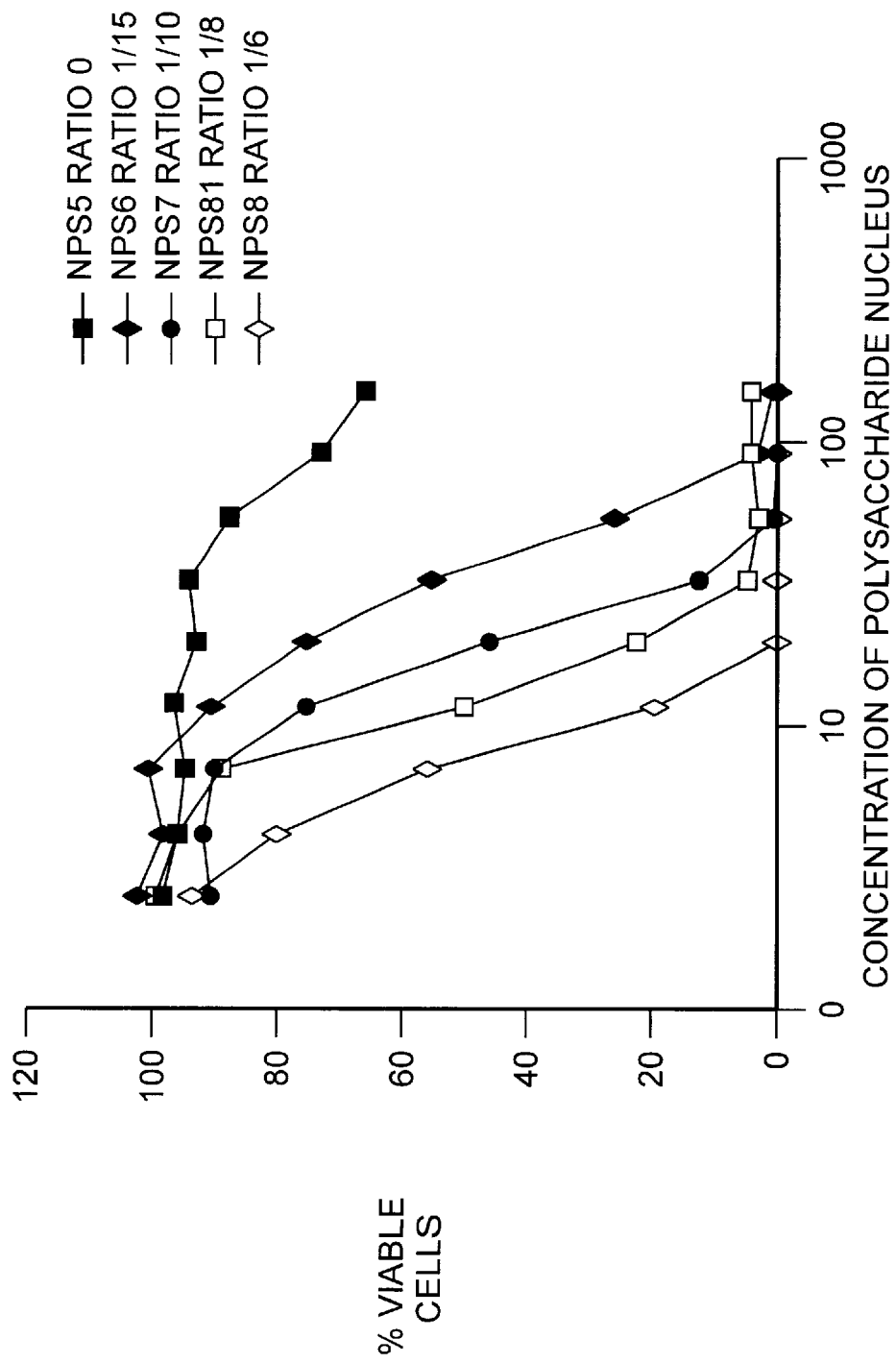
FIG. 2 EFFECT OF CROSS-LINKING RATE

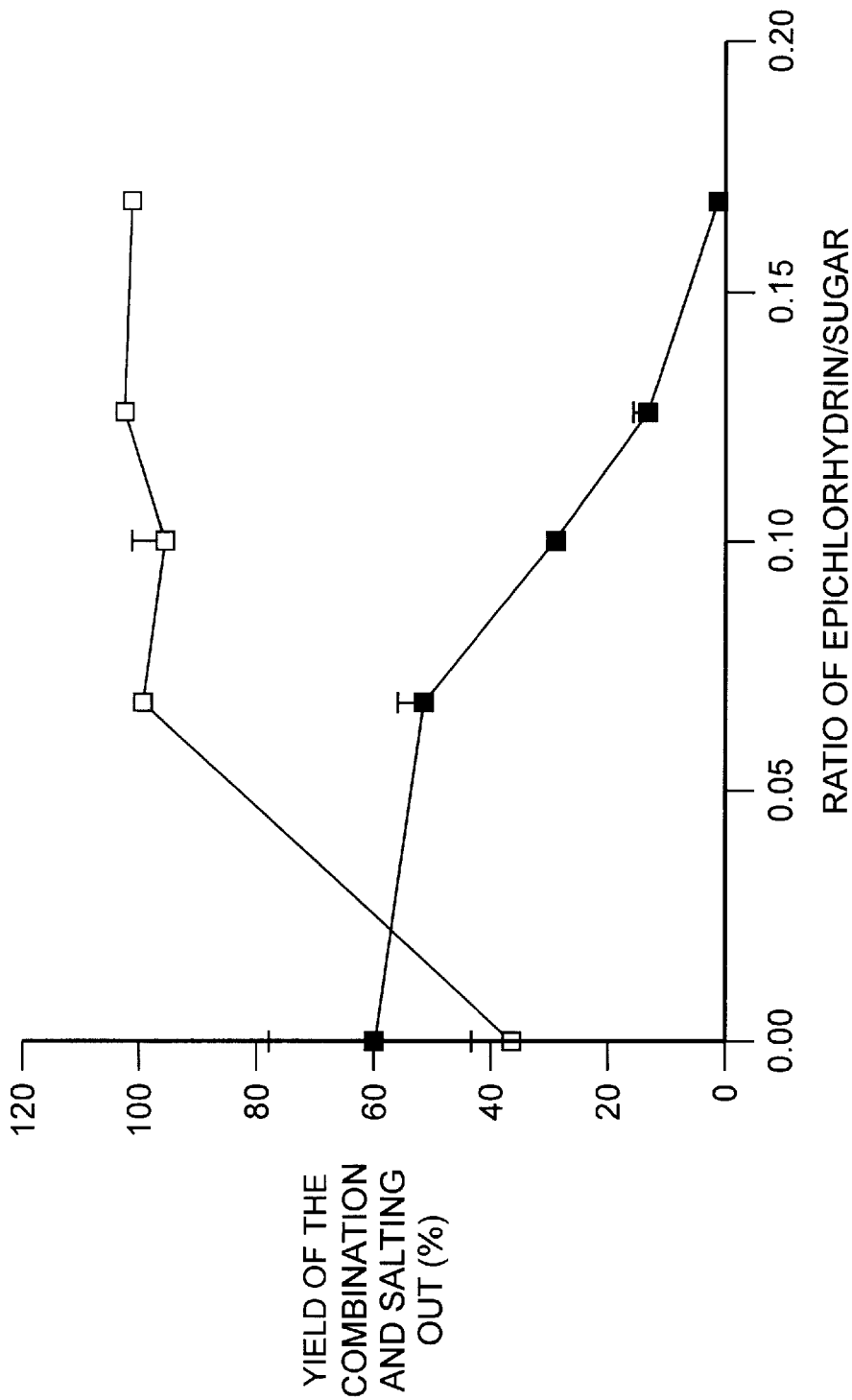
FIG. 3 EFFECT OF THE CROSS-LINKING RATE ON CHARGING

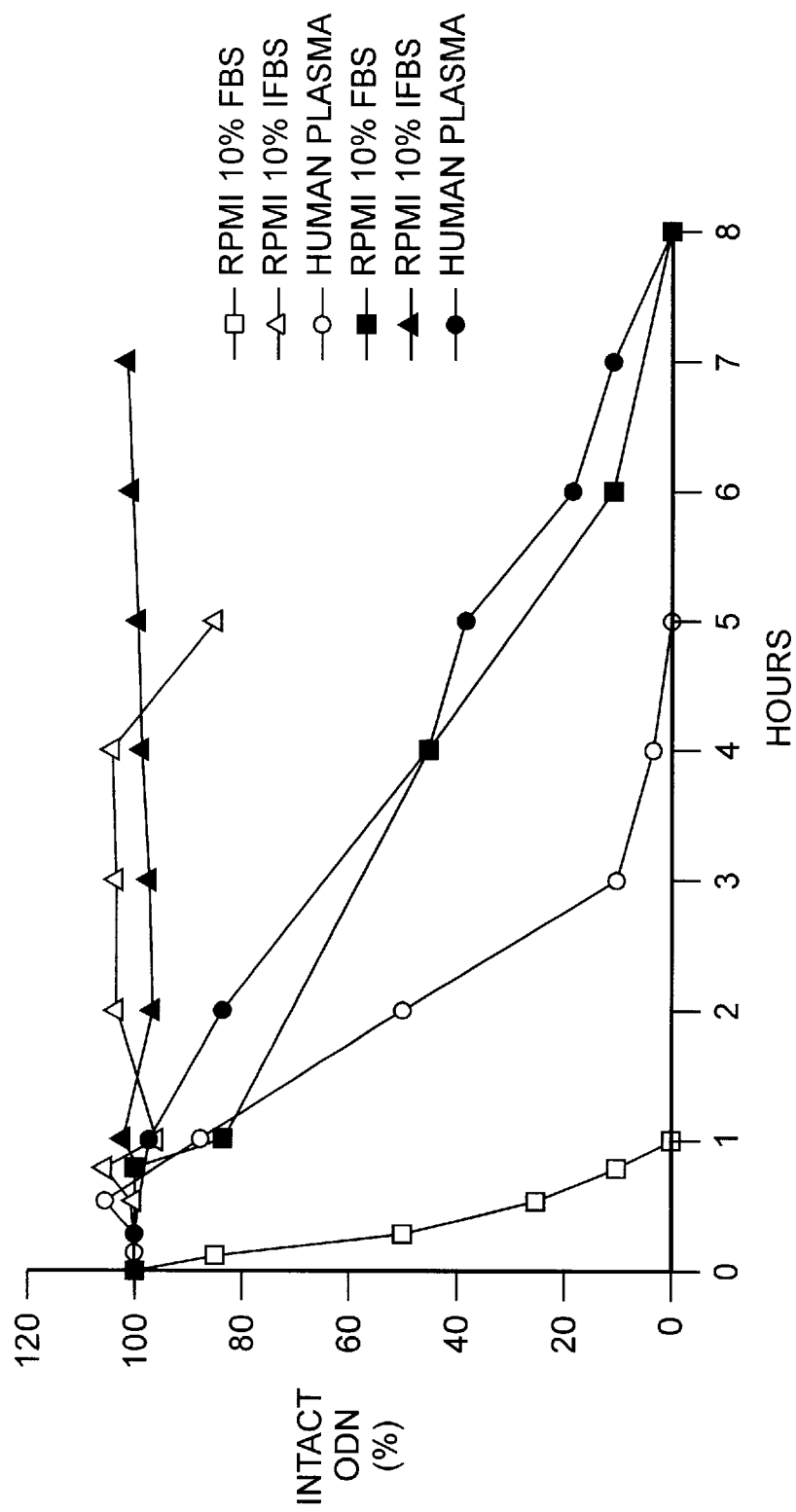
FIG. 4 PROTECTION OF ODN

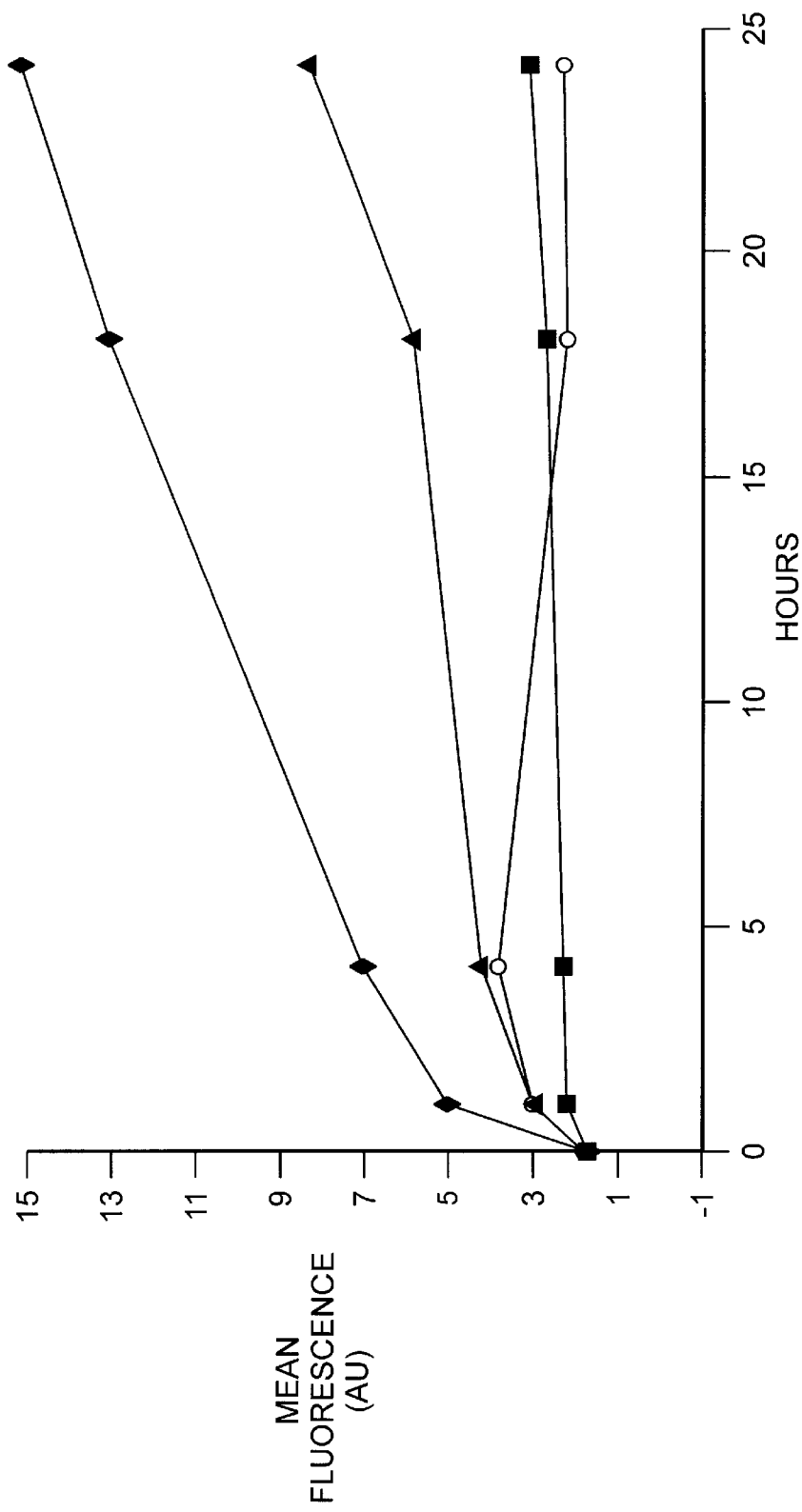
FIG. 5 ODN CELLULAR UPTAKE

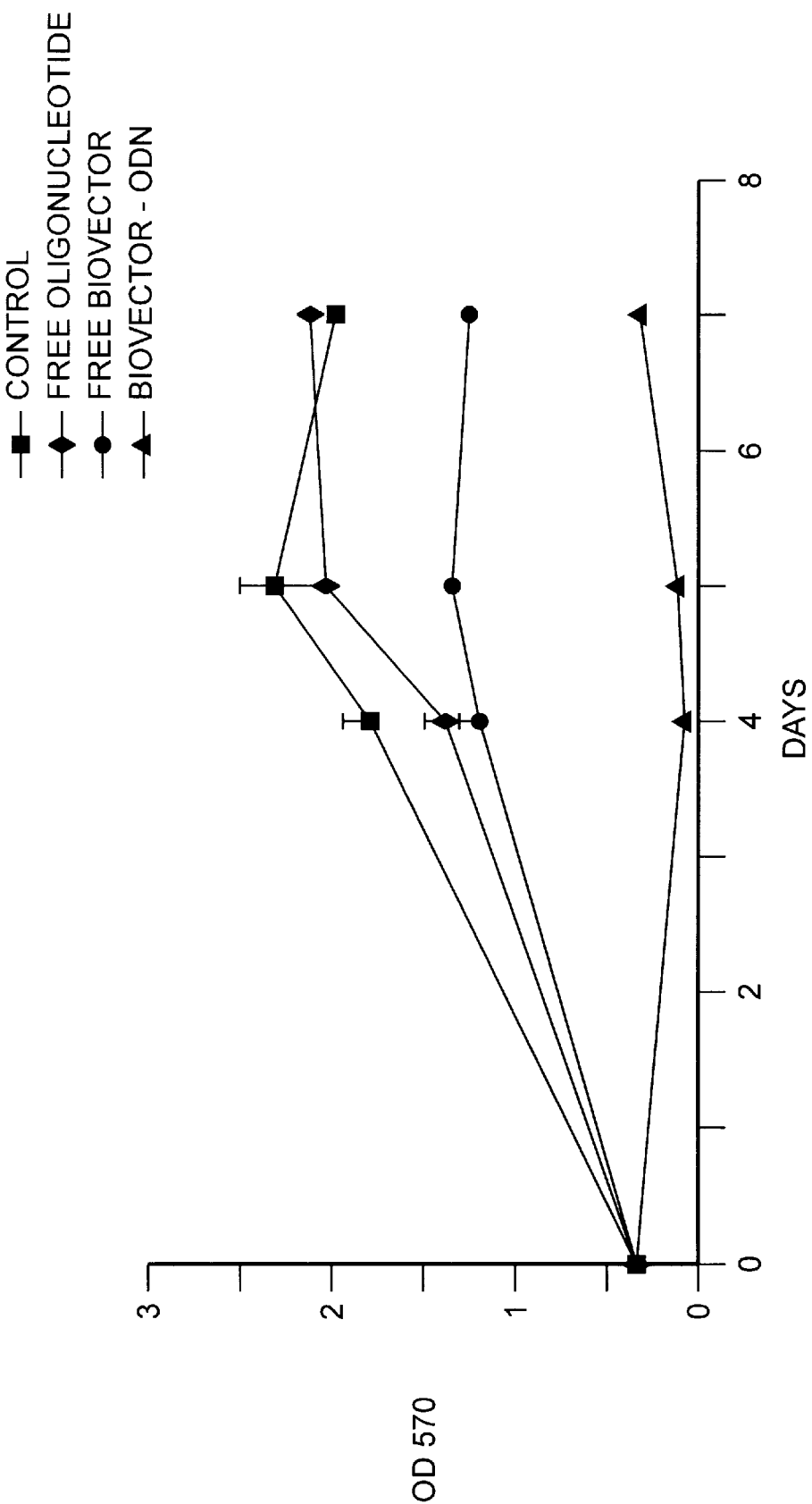

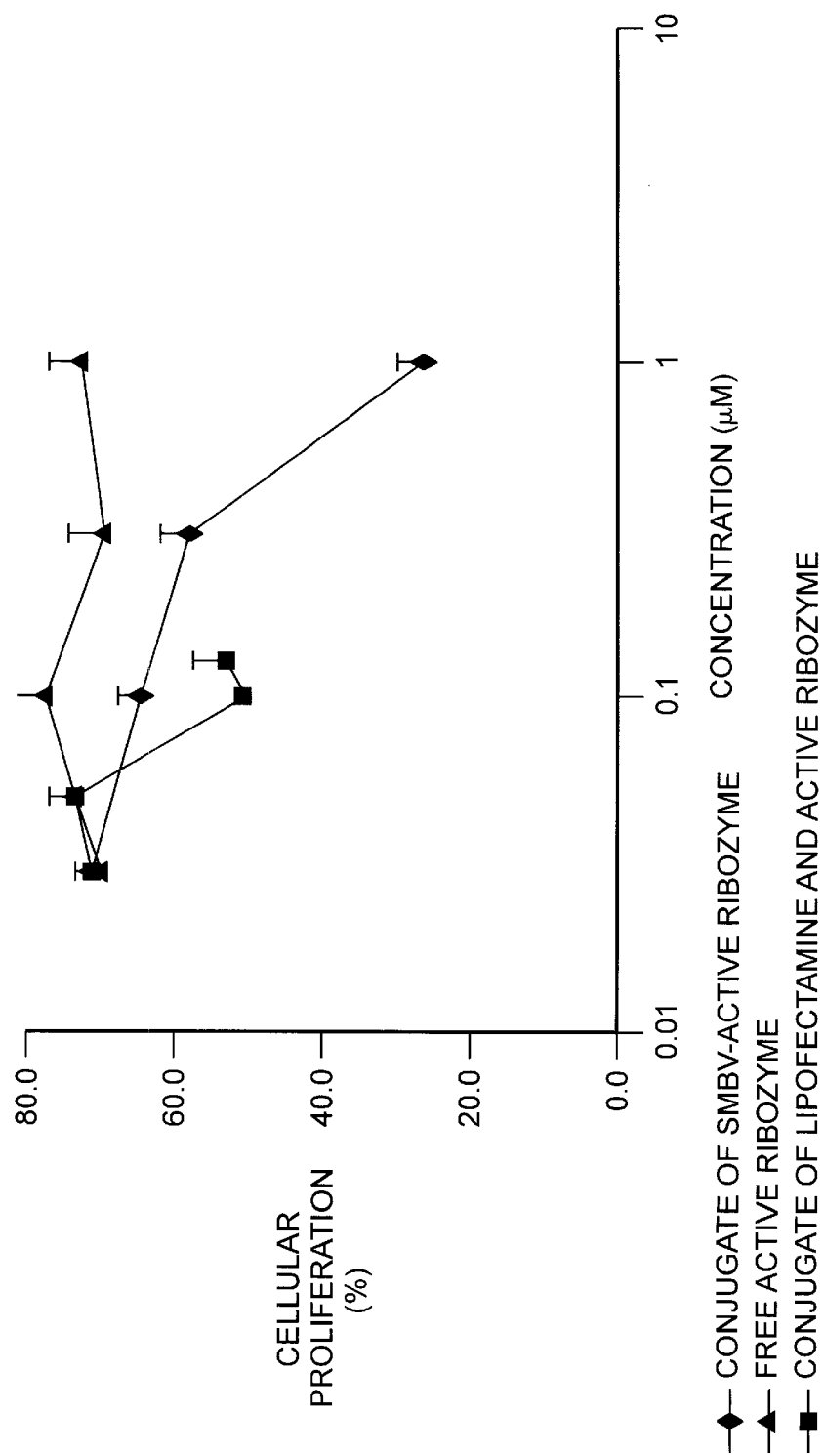

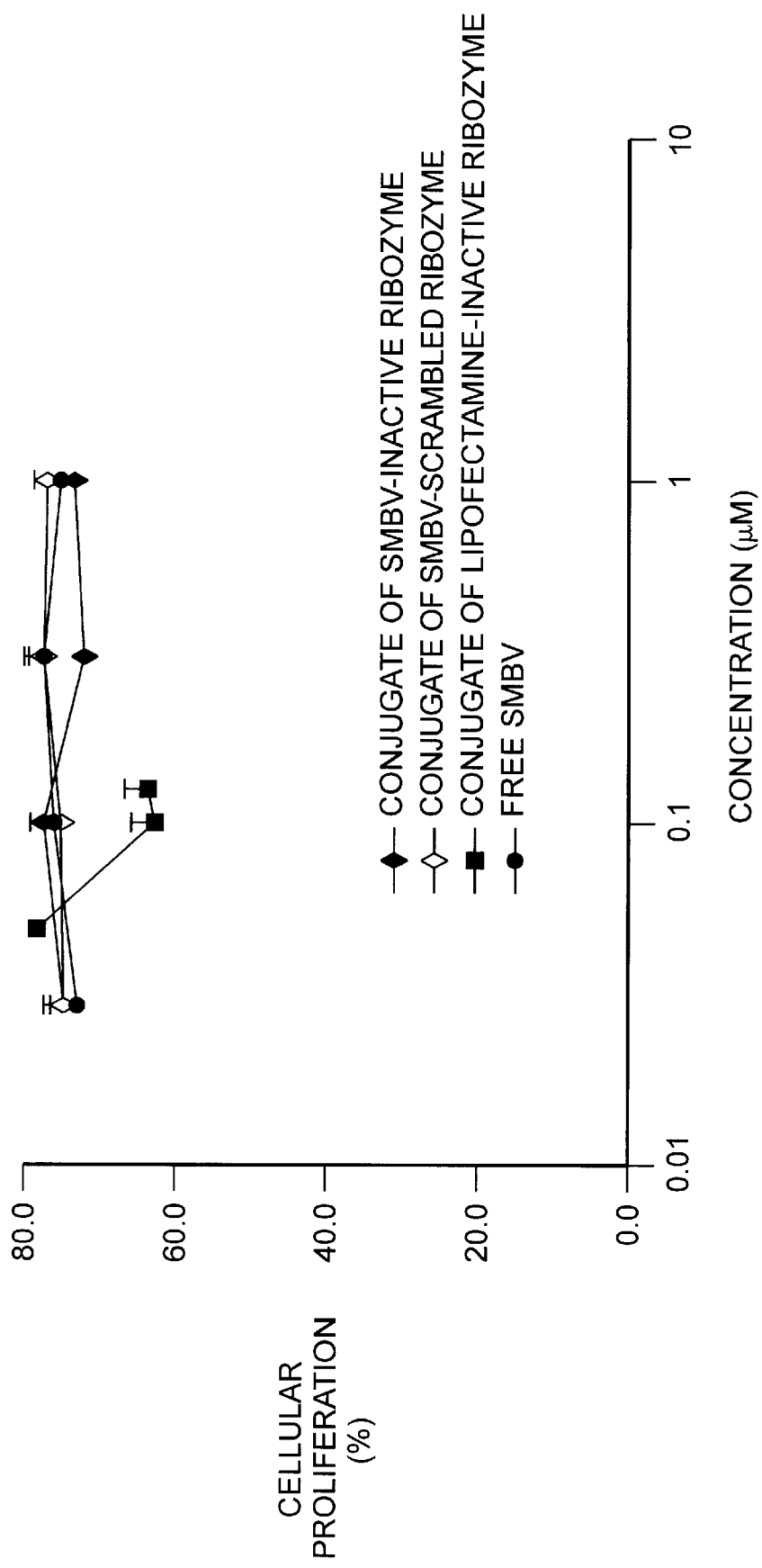

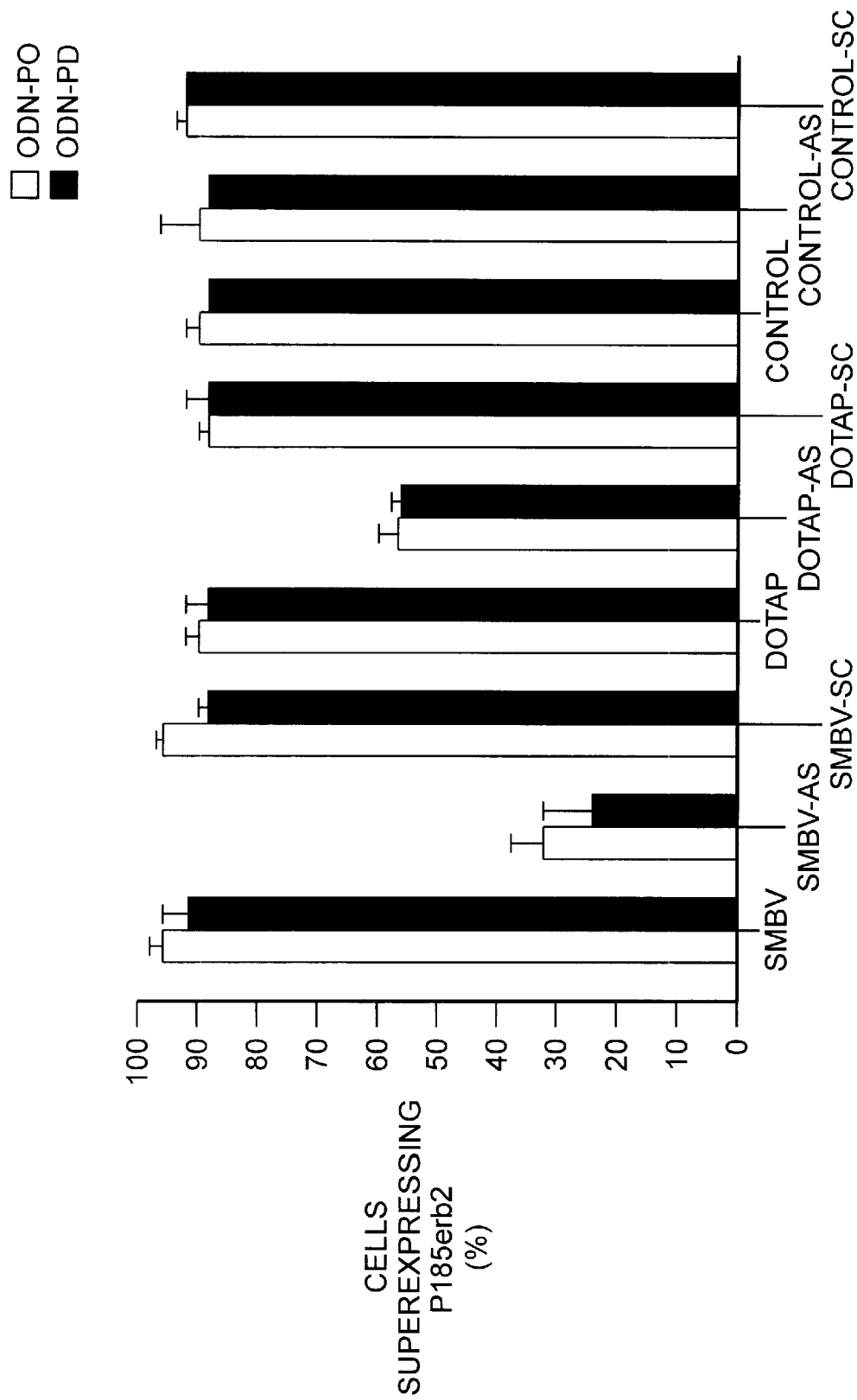
FIG. 8 EFFECT OF THE CONJUGATE ODN-BIOVECTOR ON PROTEIN EXPRESSION

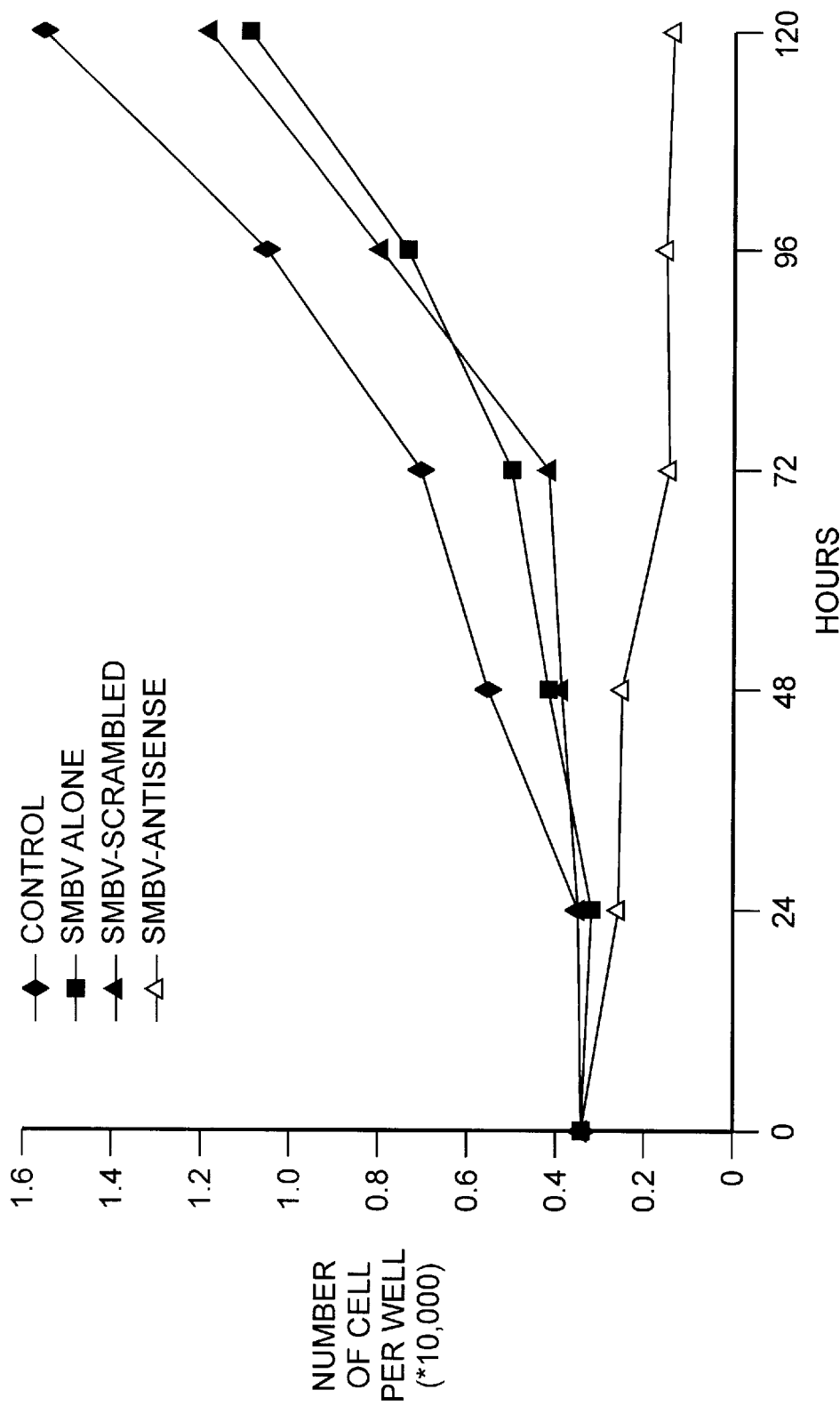
FIG. 9 CELLULAR ACTIVITY OF CONJUGATES ODN ANTISENSE-BIOVECTOR

CONJUGATES OF A PARTICLE VECTOR AND OLIGONUCLEOTIDES, PROCESS FOR THEIR PREPARATION, AND PHARMACEUTICAL COMPOSITIONS CONTAINING THEM

BACKGROUND OF THE INVENTION

This invention pertains to conjugates which make it possible to address oligonucleotides, antisense, and ribozymes, in cells. The process for their preparation, and pharmaceutical compositions containing them are also disclosed.

Oligonucleotides constitute a particularly interesting class of molecules because of their ability to form, by hybridization, specific complexes with complementary nucleic acid sequences. These complexes may include duplexes resulting from the hybridization of oligonucleotides with single-strand DNA sequences or with RNA sequences such as mRNA, and triplexes formed by hybridization with double-strand DNA molecules [1–6].

The properties cited below confer on the oligonucleotides remarkable possibilities for the study of genes, and in the area of therapeutic treatment [17]. Thus, the invention particularly pertains to antisense oligonucleotides and ribozymes, whose capacity to inhibit specifically the expression of genes on in vitro models [16,18] and the proliferation of cells in vivo [19,20], as well as the RNAse activity of the ribozymes, have already been studied.

The fixation of oligonucleotides and ribozymes on mRNA leads to the inhibition of translation of mRNA according to two general processes; on the one hand, degradation of this mRNA or the RNA/DNA duplexes by the cellular ribonuclease H (RNase H), or by the catalytic activity of the ribozymes, and on the other hand the steric blockage of the cellular machinery [1–9].

The use of chemically modified oligonucleotides makes it possible to improve their incorporation by the cell and their resistance to nucleases [10], particularly the 3'-exonucleases. Among the chemical modifications of oligonucleotides proposed in the prior art, the most promising seems to be the use of structural analogs of the phosphodiester oligonucleotides like the phosphorothioate oligonucleotides. The latter are resistant to cleavage by nucleases, and do not inhibit degradation by Rnase H [28]. These advantages have led to several cellular and pharmacokinetic studies [18,29,30], as well as to clinical tests of these compounds as antitumor and antiviral agents (31). However, the discovery of nonspecific effects has considerably limited the enthusiasm for the therapeutic use of antisense oligonucleotides (17,32,33).

In addition, a major constraint on the use of these modified oligonucleotides is that the hybridization complexes between the RNA and the oligonucleotide should be sufficiently stable so they are not dissociated by the cellular machinery. Thus, when the antisense oligonucleotides or the ribozymes are directed toward the coding region, they are separated from their target by the translation ribozymes (11–15). This dissociation can be avoided by combining the oligonucleotides with reagents that can react spontaneously, or after irradiation, with the target RNA (3–6,10,11).

For example, international patent application number WO 90/12020, proposes coupling furocoumarin to an oligonucleotide by means of a ribose or deoxyribose sugar. European Patent Application No. 316,016, International Application No. WO 89/06702, and German Patent Application No. 3,928,900 describe the use of conjugates of psoralen and oligonucleotides to block genetic expression. French Patent Application No. 2,568,254 describes the application of oligonucleotide compounds linked to an intercalating agent for the selective blockage of a nucleic acid sequence. More specifically, the application of these compounds to the selective blockage in vivo of the expression of a gene or a sequence involved in the initiation, the propagation, or the termination of the replication of a nucleic acid, the transcription of one or more genes, and/or their translation is disclosed in this French patent application.

However, these chemical methods present disadvantages because the induction of bridging by chemical agents is often accompanied by nonspecific reactions, and photochemical activation difficult to implement in vivo.

The effectiveness of the antisense oligonucleotides and ribozymes is also limited, on the one hand by their polyanionic nature, which leads to nonspecific interactions with extracellular cationic molecules [21,22] and, on the other hand, because of their weak diffusion through the plasma membrane [23–25]. To remedy these disadvantages, the prior art has proposed using, as indicated above, chemically modified oligonucleotides or transport and delivery systems [27].

The strategies of encapsulation of the oligonucleotides and ribozymes seem to constitute a better approach than the chemical modifications for favoring both transport and stability of unmodified oligonucleotides, while preserving their specificity of hybridization. Thus, the prior art conducted encapsulation of oligonucleotides in liposomes, in immunoliposomes (34,35), or pH-sensitive liposomes (36). It has been shown that encapsulation permits relative protection of the oligonucleotides against the nucleases and increases their delivery into the cells. In spite of these advantages, the encapsulation of oligonucleotides in liposomes is not entirely satisfactory, particularly because of problems in the encapsulation yield. The prior art also considers that the interaction between oligonucleotides which are conjugated to cholesterol with natural LDLs makes it possible to prolong the plasma half-life of the oligonucleotides [38] from 1 to 10 minutes, and to increase in the in vitro efficiency of antisense oligonucleotides [39]. However, the preparation of LDL from human plasma and the weak stability of the associated oligonucleotides remain major obstacles to their therapeutic use.

Cationic lipids, such as DOTMA or DOTAP, already known for DNA transfection, could also constitute transporters of oligonucleotides [40,41] and ribozymes. Their effectiveness has been demonstrated, particularly the oligonucleotide complexes and DOTAP, allowing for an increase in transport and a decrease in intra- and extracellular degradation of the oligonucleotides [41]. However, the cellular toxicity of these complexes limits their use in in vitro experiments [27,42] or for local administration [43].

More recently, the adsorption of oligonucleotides on nanoparticles of polyalkylcyanoacrylate made it possible to reinforce the protection against degradation by nucleases [44]. The inhibition of neoplastic growth in nude mice has been observed with a concentration of oligonucleotides adsorbed on these nanoparticles, 100 times weaker than with the free oligonucleotides [45]. But the possibilities for systemic use of these vehicles have not been demonstrated to date.

Therefore, there is currently no system of transport, addressing, and effective protection of the oligonucleotides, antisense and ribozymes, which would allow them to be used therapeutically.

SUMMARY OF INVENTION

The applicants have developed their expertise in the preparation of synthetic particle vectors, designated by the general term of Supramolecular Biovector nanoparticules (SMBV), or biovectors, which can fix and advantageously target different substances or active ingredients, and are therefore useful for the manufacture of pharmaceutical compositions.

A first type of supramolecular biovector, and the process for its preparation, has been described in European Patent No. 344,040.

These particles include:
- a central nonliquid hydrophilic nucleus made up of a polysaccharide or oligosaccharide nucleus, naturally or chemically crosslinked, which can be modified by various ionic groupings;
- a layer of fatty acids grafted by covalent bonds to the nucleus; and
- one or more lipid layers, made up specifically of phospholipids.

The developments of this first generation of Supramolecular Biovector nanoparticule shave led the applicants to design and prepare new Supramolecular Biovector nanoparticules with improved properties, particularly in terms of the active ingredients which are transported. The international patent applications (PCT) published under the Nos. WO 92/21329, WO 92/21330, WO 94/23701, WO 94/20078 and WO 96/06638, describe these supramolecular biovectors, their manufacture, their combination with various active principles, and their use for the preparation of pharmaceutical compositions.

The international patent applications (PCT) published under the Nos. WO 92/21329, WO 92/21330, WO 94/23701, WO 94/2278 and WO 96/06638 are incorporated herein by reference.

The combination of a Supramolecular Biovector with oligonucleotides has been mentioned in the International Patent Application PCT No. WO 92/21330, in the context of a Supramolecular Biovector having a selective tropism for a type of cell, and therefore presenting the following particular structure:
- a nonliquid hydrophilic nucleus
- a first layer, lipid in nature, linked to the nucleus by covalent bonds;
- a second layer of phospholipids linked to the first layer by hydrophobic interactions; and
- molecules of apolipoprotein B grafted onto the layer of phospholipids or protein or peptide ligands, which can specifically recognize the cellular receptors of the LDLs.

The possibility of the combination of a Supramolecular Biovector with oligonucleotides has also been presented by the inventors at the 21$^{st}$ International Symposium on controlled release of Bioactive Materials, Jun. 27–30, 1994, in Nice (France). At the time of this presentation the proposal was made that the Supramolecular Biovector nanoparticules should be used to increase the therapeutic effectiveness of unmodified oligonucleotides. The Supramolecular Biovector nanoparticules in question were of the type described in International Patent Application No. PCT WO 92/21329, i.e., made up of a nucleus of polysaccharides crosslinked by epichlorhydrin, functionalized by glycidyltrimethylammonium chloride to make positive charges appear, and covered with a first layer of fatty acids and a second lipid layer. It was proposed that the acylated nuclei be combined with the oligonucleotides by simple mixing in an aqueous medium, then creating the external lipid layer by mixing the acetylated nuclei combined with oligonucleotides with a lipid solution.

The research work carried out by the applicants since this symposium has allowed them to demonstrate, as indicated in the examples given below, that the effectiveness of a combination of a Supramolecular Biovector and oligonucleotides did not result from a simple incorporation of the oligonucleotides in the supramolecular biovector, but requires the formation of an ionic conjugate which should be stable in a biological medium presenting the ionic characteristics of the blood plasma, and allow the transport, protection, and addressing of oligonucleotides, antisenses or ribozymes, in the cells and advantageously in the cytoplasm. In addition, it was necessary to prepare conjugates whose level of combination of oligonucleotides is maximal, in order to assure the greatest effectiveness of the desired effect.

Such a stable ionic conjugate established between, on the one hand, the positive charges of the nucleus and, on the other hand, polyanionic oligonucleotides, can be obtained only if the rate of crosslinkage of the matrix and the level of positive charges of the nucleus are rigorously defined.

The studies that have led to the present invention were carried out with the applicants' understanding of the processes of making supramolecular biovectors, which allowed them to study the possibilities of modulation of the degree of crosslinkage of the polysaccharide nucleus and adjustments of the level of cationic charges of the nucleus.

Therefore, the purpose of the invention is to provide new means of transport, protection, and addressing of oligonucleotides in the cells, particularly for therapeutic purposes. This goal is reached with a new ionic conjugate, which is stable in a biological medium, of a particle vector having at least one nonliquid cationic hydrophilic nucleus and polyanionic oligonucleotides, making it possible to transport into the cells and to protect said oligonucleotides, which are capable of hybridizing with a cellular mRNA.

BRIEF DESCRIPTION OF THE DRAWINGS

FIG. 1 represents the effect of the charge density on the cytotoxicity of the cationic NPSs. Cationic NPSs having different charge densities are incubated with BL60 cells. After 72 h of incubation, the cell viability is determined by a test with MTT.

FIG. 2 represents the effect of the level of crosslinkage (ratio of epichlorhydrin/units of ose) on the cytotoxicity of the cationic NPSs. Cationic NPSs (1.4 mEq/g) having different levels of crosslinkage are incubated with HL60 cells. After 72 h of incubation, the cell viability is determined by a test with MTT.

FIG. 3 represents the effect of crosslinkage on the characteristics of the Biovector antisense conjugates. Cationic NPSs (1.4 mEq/g) having different levels of crosslinkage are conjugated to antisense. After conjugation, the combination yields (■) and the stability in PBS (phosphate buffered saline) (▲) are determined as a function of the NPS crosslinkage level.

FIG. 4 represents the degradation kinetics of the oligonucleotides in different media. Free oligonucleotides (empty symbols) or those conjugated to Biovector (solid symbols) are incubated in a culture medium which is supplemented with serum (■;__), culture medium supplemented with inactivated serum (▲;Δ) and with human plasma (●;○). After incubation, the samples are analyzed by electrophoresis (20% PAGE) and autoradiography. The quantity of undegraded oligonucleotides is expressed in percentage of the control (T0).

FIG. 5 represents the kinetics of penetration of the oligonucleotides into the cells. MCF7 cells are incubated with free oligonucleotides (■;__) or those conjugated to Biovector (▲;Δ). Two different concentrations of oligonucleotide are used: 0.8 μg/mL (__;▲) and 6.2 μg/ml (■;__). After different incubation times, the cellular penetration of the oligonucleotides was determined by flow cytometry.

FIG. 6 represents the cellular activity of the Biovector antisense conjugates. Antisense oligonucleotides targeting the c-myc oncogene (15 mers phosphorothioate) are conjugated to biovectors. These free oligonucleotides or those conjugated to the biovectors, as well as the free biovectors, are incubated with $5 \times 10^4$ HL60 cells. At different incubation times, the cellular proliferation is determined by an MTT test. The results are expressed in optical density at 570 nm.

FIG. 7a and 7b represent the cellular activity of the ribozyme/Biovector conjugates. Ribozyme oligonucleotides targeting the c-myb oncogene (35 mers) are conjugated to Biovector or to lipofectamine. These free or conjugated ribozymes (FIG. 7a), as well as different controls, inactive ribozyme Biovector conjugates, scrambled ribozyme Biovector conjugates, inactive lipofectamine ribozyme conjugate, and free Biovector (FIG. 7b) are incubated with $2 \times 10^5$ cells. The results are expressed in percentage of cellular proliferation with respect to the control (untreated cells).

FIG. 8 represents the specific inhibition of the synthesis of a protein by a phosphorothioate antisense (ODN-PO) or phosphodiester antisense (ODN-PD) conjugated to the biovectors. The inhibition of the production of P185-erb2 is measured after incubation of SK-Br3 cells with different preparations of oligonucleotides. The results are expressed in percentage of inhibition with respect to the control (untreated cells). In this figure, the abbreviations of the various preparations of oligonucleotides have the following values: SMBV=empty biovector; SMBV-AS=conjugated antisense biovector; SMBV-SC=conjugated scramble biovector; DOTAP=DOTAP alone; DOTAP-AS=conjugated antisense biovector; DOTAP-SC=conjugated scramble DOTAP; Control=cells alone; Control-AS=free antisense; Control-SC=free scramble.

FIG. 9 represents the inhibition of the proliferation of an SK-Br3 line by anti-erb2 antisense Biovector conjugates. The proliferation of SK-Br3 cells is determined after incubation of the cells with a conjugated anti-erb2 antisense of the biovectors. The results are expressed in number of cells as a function of time. The control corresponds to cells treated in the absence of oligonucleotide and biovector.

DETAILED DESCRIPTION OF THE INVENTION

More specifically, the invention pertains to a conjugate of a particle vector and oligonucleotide, characterized in that this particle vector includes at least one nonliquid hydrophilic nucleus made up of a polysaccharide or oligosaccharide nucleus, naturally or chemically crosslinked, and modified by cationic ligands, whose ratio of positive charges is between about 0.6 to about 1.8 mEq of positive charges per gram of nucleus, and the level of crosslinkage is largely the level obtained by crosslinkage with between 5 and 20 mol % epichlorhydrin per mole of ose (sugar) in the polysaccharides or oligosaccharides, and in that said particle vector is conjugated by ionic bonds which are stable in a biological medium to polyanionic oligonucleotides which are protected by said particle vector, said oligonucleotides being capable of hybridizing with a cellular mRNA.

The results reported in the examples given below show the remarkable properties of the conjugates according to the invention. Specifically, it has been observed that:

the quantity of oligonucleotides conjugated to the particle vector is at least equal to, and often much higher than, that which is possible with the simple transport systems of the prior art; in fact, on the order of 1000 copies of an oligonucleotide can be conjugated to the particle vector;

the half-life of oligonucleotides in the conjugate of the invention is increased by about 8 times with respect to that of free oligonucleotides;

the internalization of the conjugates of the invention in the cells permits about a 30-fold increase in the quantity of oligonucleotides crossing the cell membrane in a period of 5 h, and about 10 times the quantity of oligonucleotides in the cytosol of said cells.

The studies carried out by the applicants on the particle vectors and the preparation of the conjugate of the invention, have made it possible to obtain, and surprisingly so considering the speculations of the prior art, optimal combination levels and yields, since the applicants have managed, under optimal conditions, to conjugate 100% of the oligonucleotides mixed with the particle vectors. These optimal conditions are on the order of 0–0.3 g oligonucleotide per gram of vectors.

The particle vector of the conjugate of the invention comprises at least a nonliquid hydrophilic nucleus, whose size is generally between 10 nm and 5 μm inclusive, and which is preferably made up of a matrix of polysaccharides or oligosaccharides, naturally or chemically crosslinked, carrying an overall cationic charge.

The polysaccharides of the matrix comprise dextran, starch, cellulose, their derivatives and substitutes, their hydrolysis products, and their salts and esters.

An essential characteristic of the nucleus, adapted to the formation of conjugates with oligonucleotides, resides in the level of crosslinkage of the matrix. This level of crosslinkage is defined with reference to the crosslinkage capacity of a specific quantity of epichlorhydrin, which is a well-known crosslinkage agent, described in the applicants' patent applications cited above. The level of crosslinkage of the matrix allowing the creation of the conjugates of the invention is obtained by reaction with between 5 and 20 mol % epichlorhydrin per mole of ose in the polysaccharides or oligosaccharides constituting the matrix of the nucleus.

This level of crosslinkage is a determining factor for assuring the stability of the conjugate of the invention in biological fluids such as blood plasma. Without this stability, the in vivo and in vitro effectiveness of the conjugates of the invention for transporting and addressing the oligonucleotides in the target cells would be considerably decreased.

Another essential characteristic of the hydrophilic matrix of the nucleus is that it is positively ionized. This cationic ionization is obtained by grafting of ligands carrying positively charged functions onto the hydrophilic matrix.

The level of positive charges of the nucleus constitutes, like the crosslinkage rate of the hydrophilic matrix, an essential characteristic of the conjugate, on which its effectiveness depends. The cationic nature of the nucleus is, in fact, indispensable to the formation of the ionic conjugate of the invention with polyanionic oligonucleotides. But this cationic nature should be rigorously defined to assure the functionality of the conjugate in a therapeutic strategy. Thus, the research work conducted by the applicants have established that the nucleus should have between about 0.6 to about 1.8 mEq, and preferably about 0.8–1.6 mEq, of positive charges per gram of nucleus to assure an effective level of conjugation with the oligonucleotides.

The levels of crosslinkage and positive charges of the nucleus defined above are determining factors for obtaining the maximum conjugation between the vector and the oligonucleotides, and to assure the stability and the low toxicity of the conjugates of the invention.

According to a particular embodiment of the invention, the nonliquid hydrophilic nucleus is completely or partial covered by at least one layer of amphiphilic compounds. Advantageously, these amphiphilic compounds comprise natural or synthetic lipids and phospholipids, ceramides, fatty acids, glycolipids, lipoproteins and/or surfactants. In particular, the invention is focused on particle vectors whose nonliquid hydrophilic nucleus is completely or partial covered by an external layer made up:

essentially of natural or synthetic phospholipids and/or ceramides, possibly combined with other amphiphilic compounds, or natural fatty acids fixed to the nucleus by covalent bonds.

Another embodiment of the conjugate of the invention consists of using Biovector of the type described in European Patent No. 344,040, having a previously defined central nucleus, completely or partial covered by two layers of amphiphilic compounds. The amphiphilic compounds are those described previously. In this embodiment, it is preferable for the central nucleus, completely or partially covered by a first layer of fatty acids, to be itself completely or partially covered by a lipid layer.

The use of particle vectors having at least one amphiphilic layer makes it possible advantageously to combine with the conjugate of the invention an additional active principle which is useful for the transport, addressing, or presentation of the conjugate at the level of the cell membrane, in the cytoplasm or at the time of hybridization with a target mRNA. But the combination of an additional active principle may also be brought about at the level of the nucleus of the particle vector of the conjugate.

The oligonucleotides conjugated with the particle vector of the invention are natural or modified oligodeoxyribonucleotides or oligoribonucleotides, which may be labeled, having on the order of 5 bases up to one hundred bases. Such label(s) and/or modification(s) are acceptable in the framework of the invention if they do not substantially change the polyanionic nature of the oligonucleotide. The oligonucleotides conjugated to the particle vector of the invention also cover the antisense and the ribozymes. The particle vector according to the invention can be conjugated to several tens, up to about 1000 copies of the same oligonucleotide, or it may be conjugated to several oligonucleotides of different sequences, and, in this case, each oligonucleotide with a different sequence should be present in about 100 copies.

The invention also pertains to pharmaceutical compositions comprising one or more conjugates according to the invention, or their pharmaceutically acceptable salts, dispersed in pharmaceutically acceptable excipients. These pharmaceutical compositions can be administered, for example, systemically or locally, the excipients or vehicles used are chosen to be compatible with the mode of administration or application to be used.

The invention also concerns the conjugate previously defined, and is intended to be used to address an oligonucleotide in a cell, particularly in the cytoplasm.

Another object of the invention is the particle vectors used in the conjugates previously described. These particle vectors are of the type comprising at least one nonliquid cationic hydrophilic nucleus made up of a polysaccharide or oligosaccharide matrix, naturally or chemically crosslinked, carrying an overall cationic charge and having at least one of the following characteristics:

the level of crosslinkage is essentially that obtained by crosslinkage with 5–20 mol % of epichlorhydrin per mole of ose (sugar) in the polysaccharides or oligosaccharides;

said polysaccharide or oligosaccharide matrix, naturally or chemically crosslinked, is modified by cationic ligands, of which the level of positive charges is between about 0.6 to about 1.8 mEqs, and advantageously between about 0.8 to about 1.6 mEqs of positive charges per gram of nucleus.

According to a particular embodiment of the particle vector of the invention, the nonliquid hydrophilic nucleus is completely or partially covered by at least one layer of amphiphilic compounds. Advantageously, these amphiphilic compounds comprise the natural or synthetic phospholipids, the ceramides, the fatty acids, the glycolipids, the lipoproteins, and/or the surfactants. Specifically, the invention pertains to particle vectors whose nonliquid hydrophilic nucleus is completely or partially covered by an external layer comprising:

essentially natural or synthetic phospholipids and/or ceramides, possibly combined with other amphiphilic compounds, or natural fatty acid fixed to the nucleus by covalent bonds.

The results reported in the examples below show that a particle vector comprising at least one nonliquid cationic hydrophilic nucleus can be used advantageously to address the oligonucleotides to the cytoplasm of a cell.

As previously indicated, the oligonucleotides addressed in the cytoplasm of a cell are oligoribonucleotides or oligodeoxyribonucleotides, antisense or ribozymes, possibly labeled, natural or modified since the labeling or modification does not substantially change the polyanionic nature of the oligonucleotides.

The invention also pertains to processes for preparation of the ionic conjugates defined above. In fact, the processes described in the prior art do not allow for obtaining conjugates having all the required properties for an antisense or ribozyme strategy. Research studies conducted by the applicants on the preparation of conjugates have allowed them to define processes making it possible to obtain functional conjugates in a reproducible manner.

Such a process is characterized in that it comprises the following stages:

a) the preparation of the cationic nucleus:

by mixing a hydrophilic polymer, polysaccharide or oligosaccharide in nature, chemically or naturally crosslinked with a crosslinkage agent in a ratio between 0.06 and 0.2 mole, preferably 0.1 and 0.15 mole of crosslinkage agent per unit of ose (sugar) in the polysaccharide or oligosaccharide.

by adding to the above mixture a cationic ligand to obtain a level of charge of the nucleus between about 0.6 to about 1.8, and preferably between about 0.8 to about 1.6 mEq per gram of nucleus;

b) charging of the polyanionic oligonucleotides:

by adding, under agitation, to the nucleus prepared in stage (a), between about 0.02 to about 0.4 g, and preferably between about 0.05 to about 0.2 g, of oligonucleotide per gram of nucleus, at a rate from about 0.25 µg of oligonucleotide per mg of nucleus per hour, to about 6 mg per mg of nucleus and per hour, and preferably between about 4 μg/mg/h to about 1 mg/mg/h, at a temperature between about 20° C. and 60° C., and preferably between about 40° C. and 50° C.

According to the type of particle vector entering into the composition of the conjugate of the invention, the above process may include adjustments in stage (a).

For preparation of the particle vector whose nucleus is completely or partially covered by one or two layers of amphiphilic compounds, stage (a) also includes grafting onto the nucleus or the underlying layer of a layer made up of amphiphilic compounds.

The grafting may be:
a layer of fatty acids, linked to the nucleus by covalent bonds, and/or
a thin external sheet capable of modifying the cellular behavior of the conjugate of the invention made up, for example, of zwitterionic phospholipids which may or may not be combined with anionic and/or cationic lipids, linked to the underlying layer or to the nucleus by hydrophobic and/or ionic and/or hydrogen bonds.

A preferred embodiment of stage (b) of the process of the invention consists of adding to the particle vectors prepared according to stage (a), of which the concentration expressed in cationic nucleus is between about 1 to about 20 mg/mL, a solution of oligonucleotides at a concentration between about 1 to about 20 mg/mL, to obtain a ratio of oligonucleotides/particle vectors between about 2 to about 40%, and preferably between about 5 to about 20%, according to an addition kinetics of the oligonucleotide solution between about 5 μL/mL/h to about 300 μL/mL/h, and an incubation temperature between about 20° C. to about 60° C., preferably between about 40° C. to about 50° C.

Other advantages and characteristics of the invention will appear from the following examples, which concern the preparation and use of the particle vectors and the conjugates of the invention, and which refer to the drawings.

EXAMPLE 1

Preparation of Cationic Polysaccharide Nuclei Having Different Levels of Charge

In a 3 L reactor, we solubilize 100 g Glucidex 2 (Roquette, France) in 0.2 L 2N NaOH. When the solution is homogeneous, we introduce the crosslinking agent, epichlorhydrin (Fluka, Switzerland) with a molar ratio (mole of epichlorhydrin/mole of glucose unit) of 10%. After the addition is completed, the preparation is maintained under agitation for 12 h at 20° C. We then add glycidyl trimethylanunonium Chloride (GTMA, Fluka, Switzerland). To obtain different levels of charge, several molar ratios of GTMA/glucose unit are used (Table I). When all the GTMA is added, the preparation is left under agitation for 8 h at 20° C. The resulting ionic gel is then dispersed in 2 L of osmosis water, neutralized with acetic acid, and homogenized with a Rannie homogenizer (type Minilab 8:30) at a pressure of 1000 bars.

The resulting polysaccharide nuclei (NPS) are ultrafiltered on a 30 kd membrane (Incelltech, France) and filtered on a 0.45 μm cartridge (Millipore, France).

In Table I, the level of charge of the NPSs obtained is determined by elementary analysis of the level of nitrogen present in tie gel.

TABLE I

| Number | Ratio of GTMA/Unit of Glucose (%) | Final Charge (mEq/g) |
| --- | --- | --- |
| NPS-1 | 26 | 0,8 |
| NPS-2 | 29 | 1,0 |
| NPS-3 | 38 | 1,2 |
| NPS-4 | 50 | 1,4 |

Thus, by adjusting the initial ratio of GTMA/glucose unit, it is possible to modulate the charge density of the cationic NPSs.

These studies, and those carried out on other polysaccharides, have made it possible to demonstrate that it is possible to modify the charge density of the NPSs in a range of 0–2 mEq/g corresponding to a ratio of GTMA/glucose unit of 0–70%. For the synthesis of the conjugates of the invention, it is preferred that the charge be between about 0.6 to about 1.8 mEq/g, most preferably between about 0.8 to about 1.6 mEq/g.

EXAMPLE 2

Preparation of Cationic Polysaccharide Nuclei Having Different Levels of Crosslinkage Table II shows the different cationic NPSs prepared according to Example 1 with variable molar ratios of epichlorhydrin/glucose unit and a constant ratio of GTMA/glucose unit (50%), permitting a charge of 1.4 mEq/g of gel.

TABLE II

| Number | Ratio of Epichlorhydrine/Unit of Glucose (%) |
| --- | --- |
| NPS-5 | 0 |
| NPS-6 | 6,7 |
| NPS-7 | 10,0 |
| NPS-8 | 12,5 |
| NPS-9 | 16,7 |

These studies, and those conducted on other polysaccharides, have allowed us to demonstrate that the ratios which can be used are between 0 and 20%, corresponding to the modification of one glucose unit out of five. For preparation of the conjugates of the invention, the ratio is between 6 and 20%, preferably between 10 and 15%.

EXAMPLE 3

Preparation of the Supramolecular Biovector Called "SMBV-Iight"

The preparation of Biovector occurs in two principal stages: (1) the synthesis of the cationic polysaccharide nuclei, (2) the combination of lipids with the NPSs, called the synthesis of the Biovector (light type).

(1) Synthesis of the cationic NPSs

A quantity of 500 g Glucidex maltodextrins (ROQUETTE) is solubilized with 0.880 L water in a thermostat-controlled reactor at 20° C. under agitation. We then introduce about 7 g NaBH₄ and agitate it for 1 hour.

A quantity of 220 mL 10 M NaOH is added, followed by 30.25 mL epichlorhydrin (Fluka). After 12 h of reaction, 382.3 g glycidyltrimethylammonium chloride (Fluka) is introduced, and the mixture is kept under agitation for 10 hours.

The gel is diluted with 8 L of demineralized water and neutralized with glacial acetic acid.

The hydrogel obtained is ground in a high-pressure homogenizer (RANNIE Lab). The pressure exerted is 400 bars. At the end of this stage, the dispersed matrices have an average diameter of 60 nm.

Purification is carried out by the successive stages of:

0.45 µm microfiltration to eliminate the particles which are too large, and diafiltration at constant volume to eliminate the small molecules (salts, polysaccharide fragments).

Finally, the NPSs are concentrated, recovered in sterile bottles, and stored at −20° C.

(2) Synthesis of biovectors

The thawed cationic polysaccharide nuclei are diluted with osmosis water in a glass container in a proportion of 1 mg NPS/1 mL of water. In the first step, the dispersion is put under magnetic agitation (5–10 min) then homogenized (RANNIE Minilab) at 400 bars for 3 min. The dispersion of NPS is placed in a water bath at 80° C.

The lipids (example: mixture of egg yolk lecithin/cholesterol), in powder form, are weighed so that the total weight represents, for example, 20% (w/w) of the weight of the NPSs. The lipids making up the membrane are mixed and solubilized with 2 mL 95% ethanol (v/v). The charged lipids represent, for example, 5% (w/w) of the total lipids.

The homogenizer is brought to a minimum temperature of 60° C. by circulation of water in a closed circuit.

Concomitantly, the NPSs dispersed at 80° C. undergo magnetic agitation, and the ethanolic lipid solution is injected into the NPS dispersion.

The water for heating the circuit of the homogenizer is evacuated and replaced by the "NPS/lipids" dispersion at 80° C. This new dispersion is homogenized at 450 bars for 25 min in a closed circuit at a minimum of 60° C. At the end of this stage, the preparation is introduced into a glass flask, then subjected to low pressure at 60° C. to eliminate the ethanol remaining in solution. If necessary, the Biovector obtained can be concentrated by ultrafiltration, lyophilization, or evaporation.

The resulting cationic Biovector are then stored under sterile conditions after filtration on 0.2 µm.

EXAMPLE 4

Preparation of the Supramolecular Biovector Called "Complete SMBV"

The preparation of a complete SMBV is as described in European Patent Application No. 344,040, with egg yolk lecithin/cholesterol (80/20 w/w), ratio of lipid/NPS 100%.

In this embodiment, we prepare the NPS Supramolecular Biovector nanoparticules of Example 3, which then undergo an acylation phase to obtain acylated NPSs. After phospholipidation, we obtain complete SMBVs.

EXAMPLE 5

Cytotoxicity of the Cationic Polysaccharide Nuclei

Protocol

Different suspensions of cationic NPSs are diluted in a cell culture medium (RPMI 1640, Gilco, France). The resulting suspensions are then mixed with an equivalent volume of cellular suspension (100 µL of HL60 cells with $5 \times 10^4$ cells/mL). The cell suspensions prepared in this way are incubated for 72 h at 37° C. in an incubator with 5% $CO_2$.

After incubation, the cells are washed in PBS (10 mM $Na_2HPO_4/NaH_2PO_4$, 130 mM NaCl, 2 mM KCl, pH 7,4), and the cell viability is determined by a test with MTT.

Each result is the average of two independent experiments conducted on six experimentation points.

a) Effect of the charge of the polysaccharide nuclei

The NPSs of Example 1 (initial ratio of epichlorhydrin/glucose unit of 10%) were used to show the effect of charge on the cytotoxicity of the cationic NPSs.

FIG. 1 shows the response curve obtained on the HL60 line and for charge densities between 0.8 and 1.4 mEq/g. It appears that the cellular toxicity of the NPSs is observed for concentrations between 10 and 150 µg/mL (IC20 after 3 days of incubation). However, this can be adjusted by the density of cationic charges of the NPSs.

b) Effect of crosslinkage rate

FIG. 2 shows the cytotoxicity curves obtained with the HL60 cells and the cationic NPSs of Example 2. For this charge density (1.4 mEq/g) and for crosslinkage rates varying from 0 to 16.7%, the cellular toxicity is observed for concentration between 10 and 150 µg/mL inclusive (IC20). As is true for the charge effect, the crosslinkage appears as an important parameter of the cellular toxicity of the cationic NPSs.

c) Synergistic effect of the charge and the crosslinkage rate

Table III, below, summarizes the cytotoxicity results observed on the HL60 line after 72 h of incubation for different cationic NPSs which differ by their charge density and their crosslinkage rate. The results are expressed in IC20, concentration of NPS which inhibits 20% of the cellular proliferation 72 h after incubation.

TABLE III

| Number | Polysaccharide | Crosslinkage Rate (%) | Charge (mEq/g) | IC20 (µg/ml) |
|---|---|---|---|---|
| NPS-1 | Glucidex 2 | 10,0 | 0,8 | >150 |
| NPS-2 | Glucidex 2 | 10,0 | 1,0 | 90 |
| NPS-3 | Glucidex 2 | 10,0 | 1,2 | 48 |
| NPS-4 | Glucidex 2 | 10,0 | 1,4 | 12 |
| NPS-5 | Glucidex 2 | 0 | 1,4 | 76 |
| NPS-6 | Glucidex 2 | 6,7 | 1,4 | 17 |
| NPS-7 | Glucidex 2 | 10,0 | 1,4 | 10 |
| NPS-8 | Glucidex 2 | 12,5 | 1,4 | 8 |
| NPS-9 | Glucidex 2 | 16,7 | 1,4 | 4 |
| NPS-10 | Tackidex | 12,5 | 1,9 | 3 |
| NPS-11 | Tackidex | 12,5 | 1,6 | 5 |
| NPS-12 | Tackidex | 20,0 | 0,5 | >150 |
| NPS-13 | Glucidex 6 | 20,0 | 0,7 | 36 |
| NPS-14 | Glucidex 2 | 12,5 | 0,8 | >150 |
| NPS-15 | Glucidex 2 | 0 | 1,0 | >150 |

These results indicate that there is a synergistic effect between the cytotoxicity induced by the charge density and by the crosslinkage rate of the cationic NPSs. Thus, it is possible to adjust the cellular toxicity of the cationic NPSs by adjusting the conditions of synthesis of these NPSs.

For the preparation of the oligonucleotide/Biovector conjugates, the search for a minimum toxicity and a maximum combination yield should lead to a compromise. This can be brought about for charges between 0.8 and 1.6 mEq/g, and crosslinkage rates of 10–15%.

EXAMPLE 6

Charging of Oligonucleotides in Cationic NPSs

Methods

A solution of oligonucleotide (antisense of 15mer) at 2.5 mg/mL in water is slowly added (5 µL/mL every h) to a solution of cationic NPSs at 1 mg/mL, kept at 45° C. under magnetic agitation. Thus, the ratio of oligonucleotide/NPS is 5% (w/w). After the last addition of oligonucleotide, the preparation is incubated for 1 h under magnetic agitation at 45° C.

The concentration of free oligonucleotides is determined by spectrophotometry after ultrafiltration of the preparations. Similarly, in order to determine the stability of the complex with respect to ionic strength, the preparation is incubated in PBS (10 mM NaH$_2$PO$_4$/Na$_2$HPO$_4$, NaCl 130 mM, KCl 2 mM, pH 7.4). After this incubation (30 min at 37° C.), the free oligonucleotides and those associated with the NPS are separated by ultrafiltration, and the concentration is determined by spectrophotometry.

a) Effect of the charge of the cationic NPSs

Table IV, below, summarizes the results of the combination obtained for different charges of the cationic NPSs (0.6, 0.9, and 1.6 mEq/g), and shows the influence of charge of the cationic NPSs on the combination yields and the stability in PBS of the oligonucleofide-NPS complexes.

TABLE IV

|  | 0,6 mEq/g (n = 9) | 0,9 mEq/g (n = 2) | 1,6 mEq/g (n = 9) |
| --- | --- | --- | --- |
| Combination yield (%) | 61,8 ± 11,5 | 80,2 ±12,4 | 89,7 ±6,0 |
| Free ODN after PBS (%) | 73 ± 14 | 78 ± 8 | 46 ± 9 |

The results obtained indicate that there is a close relationship between the charge of the NPSs and the quality of the NPS-oligonucleotide conjugates measured by the combination yields and their stability after incubation in PBS.

b) Effect of the crosslinkage rate

FIG. 3 shows the results obtained when the NPSs of example 2 are used in the combination protocol.

These results indicate that, for the charge used, 1.4 mEq/g, the crosslinkage rate has little influence on the combination yields. On the other hand, the increase in the ratio of epichlorhydrin/unit of glucose permits a progressive improvement in the stability of the complex after incubation in PBS.

Thus, the optimum NPS synthesis for the formation of the conjugates should correspond to a compromise between the charge density of the NPS and the crosslinkage of the polysaccharide in order to maximize the qualities of the oligonucleotide-Biovector conjugate and to minimize their cellular toxicity.

EXAMPLE 7

Obtaining a Nonaggregating Protocol in the Preparation of Oligonucleotide-Biovector Conjugates Biovector prepared as in Example 4 are conjugated to oligonucleotides (antisense of 18 mers) using the protocol described in Example 6 with an oligonucleotide/NPS ratio of 10%. However, the energy contribution is made by two methods:

Method 1: The oligonucleotides are added to an ultrasound bath at ambient temperature.

Method 2: The addition of the oligonucleotides is made under magnetic agitation at 45° C.

Method 1 results in an aggregation of the biovectors, indicating that the ultrasound is not sufficient to dissociate the biovector/oligonucleotide aggregates. On the other hand, method 2 results in a protocol of nonaggregating conjugation, making it possible to obtain homogeneous suspensions.

EXAMPLE 8

Preparation of a Conjugate of Oligonucleotide and Biovector

Table V, below, shows the characteristics of the oligonucleotide-Biovector conjugates obtained by using an antisense oligonucleotide (oligodeoxynucleotide-(ODN) with 15 mers) or a ribozyme (oligoribonucleotide-(ORN) with 35 mers), and the Biovector described in Example 3, whose NPSs have defined characteristics (for example, a charge of 0.8 mEq/g and a crosslinkage rate of 12.5%).

The combination protocol used corresponds to the protocol of Example 6. However, the solution of oligonucleotides is added at a rate of 10 µL/mL every hour for 4 h of incubation. Thus, the ratio of oligonucleotide/NPS is kept at 10%.

TABLE V

|  | Ribozyme | Antisense |
| --- | --- | --- |
| Combination yield (%) | 98,0 ± 2,0 | 99,3 ± 2,1 |
| Free oligonucleotide after PBS (%) | 9,3 ± 3,6 | 5,3 ± 3,5 |
| Filterability (%) | 95,0 ± 2,4 | 98,2 ± 2,4 |
| Mean diameter (nm) | 89 ± 3 | 85 ± 5 |

The results show that the nature of the oligonucleotides, particularly their size (number of-mers) and their structure (antisense versus ribozyme), has little influence on the characteristics of the oligonucleotide-Biovector conjugates. In addition, these results confine that the combination protocol used, which is a nonaggregating protocol, makes it possible to obtain conjugates which can be sterilized by filtration on a 0.2 µm membrane.

Thus, in a conjugation protocol using:

Biovector at a concentration expressed in cationic NPS, between about 1 to about 20 mg/mL inclusive, oligonucleotides (for example, antisense oligonucleotides, or ribozymes) at a concentration between about 1 to about 20 mg/mL, a ratio of oligonucleotide/cationic NPS between about 2 to about 40%, preferably between about 5 to about 20%, an addition kinetics of the oligonucleotide solution between about 5 µL/mL/h to about 300 µL/mL/h, an incubation temperature between about 20° C. to about 60° C., preferably between about 40° to about 50° C.

we obtain conjugates of the invention with remarkable functional characteristics.

EXAMPLE 9

Protection of the Oligonucleotides after Conjugation with Biovectors

Oligonucleotides (phosphodiester, 15 mers, Genset, France) are labeled with phosphorus 32 by the following method: labeling of the 5'-end with ATP-[g$^{32}$p] by T4 polynucleotide kinase (Boehringer Mannheim, France), followed by purification on an exclusion column.

These free nucleotides or those conjugated with Biovector (ratio of oligonucleotide/NPS 10%) are incubated at a concentration of 6.25 µg/mL in different media:

RPMI 1640+10% fetal calf serum

RPMI 1640+10% inactivated fetal calf serum (negative control)

Human plasma

At different times, the samples are taken, heated to 65° C. to destroy the nuclease activities, and stored at 4° C. until they are analyzed. The samples are analyzed by electrophoresis on acrylamide gel (20%). The gels are autoradiographed and quantified on a Kodak DSC 200 system.

FIG. 4 shows that the conjugation of the oligonucleotides to the Biovector makes it possible to obtain effective protection against the nucleases. In fact, the free oligonucleotides are rapidly degraded in media containing active serum. Thus, in these media, the degradation of the free oligonucleotide is complete after 45 min of incubation. On the other hand, after conjugation to the biovectors, the complete degradation of the oligonucleotides is obtained after 6–8 h of incubation.

The same type of profile can be obtained after incubation in human plasma, with the half-life increasing from 120 to 225 min. respectively, for the free oligonucleotide and that conjugated to the biovectors.

EXAMPLE 10

Cellular Penetration of the Olizonucleotide/Biovector Conjugates

Biovector/oligonucleotide conjugates are prepared with an oligonucleotide labeled with fluorescein (phosphodiester, 18 mers, Genset, France). The oligonucleotides, either free or conjugated to biovectors, are incubated with $2\times10^5$ MCF7 cells human breast cancer) at a concentration of 0.78 and 6.25 µg/mL.

After incubation of the cells at 37° C., they are collected by trypsinization and washed in PBS. The cells are then incubated for 40 min in monensin (20 µm) and analyzed by flow cytometry with an excitation laser at 488 nm and an emission filter at 530 nm (Becton Dickinson, France). The results are expressed in arbitrary units of fluorescence obtained per $10^4$ living cells.

FIG. 5 shows the results obtained, and also shows the capacity of the Biovector to increase the cellular penetration of the oligonucleotides. In particular, it has unexpectedly been found that the cellular penetration of the oligonucleotides is extremely weak. On the other hand, an effective cellular penetration of the oligonucleotide can be obtained after conjugation to the biovector. This penetration is linked to the concentration in oligonucleotide-Biovector conjugate and to the incubation time of the conjugate and the cells.

The combination of these properties of the oligonucleotide-Biovector conjugate, stabilization of the oligonucleotide to the action of nucleases and cellular penetration, is certainly the important point for improving the biological activity of the oligonucleotides in the antisense and ribozyme strategies.

EXAMPLE 11

Activity of the Antisense-Biovector Conjugates on the HL60 line

Biovector are prepared by the protocol described in Example 3, whose NPSs have defined characteristics (for example, a charge of 0.8 mEq/g and a crosslinkage rate of 12.5%).

An antisense targeting the mRNA of the oncogene c-myc (phosphorothioate 15 mers, Lynx Therapeutics, California) is conjugated to these Biovector according to the protocol described in Example 6, with a ratio of oligonucleotide/NPS of 5%.

The unconjugated biovectors, the free ogligonucleotide or the one conjugated to the biovectors, are incubated at 37° C. with $5\times10^5$ cells (HL60 line) at the concentration of 1 µM in the culture medium (RPMI 1640+10% fetal calf serum). At different times, the cells are sampled, washed in PBS, and the cellular proliferation is determined by a test with MTT.

The results reported in FIG. 6 show a clear improvement in the antisense activity, which is expressed by an inhibition of the cellular proliferation over time. It is important to note that, for the concentration used (1 µM), the free oligonucleotide is not capable of expressing this activity. On the other hand, the oligonucleotide-Biovector conjugates in these conditions make it possible to inhibit cellular proliferation for the five days of the experiment.

Since the oligonucleotide used in these experiments is a phosphorathioate oligonucleotide, which is by nature resistant to the nucleases present in the culture medium, this improvement in the antisense activity seems to be due to the increase in the cellular concentration in oligonucleotides.

EXAMPLE 12

Cellular Activity of the Biovector Ribozyme Conjugates

Biovector are prepared according to the protocol described in Example 3, whose NPSs have defined characteristics (for example, a charge of 0.8 mEq/g and a crosslinkage rate of 12.5%).

Ribozymes targeting the mRNA of the c-myb oncogene (Ribozyme Pharmaceutical, Inc., Boulder, CO) are conjugated to these Biovector according to the protocol described in Example 6 with a ratio of oligonucleotide/NPS of 5%. In addition, three negative controls are prepared under the same conditions, an inactive ribozyme conjugate, a ribozyme incapable of making the catalytic cut of the mRNA, a conjugate of scrambled ribozyme, a ribozyme incapable of recognizing the c-myb sequence, and empty biovectors. By comparison with the prior art, the active and inactive ribozymes are conjugated to lipofectamine.

In these experiments, $2\times10^5$ RSMC cells (rat smooth muscle cells) are incubated in a culture medium without serum (Optimem). After 48 h of incubation, 100 µL Optimem containing variable concentrations of ribozymes are added to the cells. After a new incubation period of 24 h (3 h for the lipofectamine), the cellular proliferation is stimulated by placing the cells in a culture medium supplemented with 10% fetal calf serun. The cellular proliferation is determined by a test with 5-bromodeoxyuridine (BrdU).

FIGS. 7a and 7b show the response curve obtained for the ribozyme-Biovector conjugates and the ribozyme-lipofectamine conjugates, as well as for various controls, empty Biovector or conjugated with inactive ribozymes. Under the same conditions, the active or inactive ribozymes not conjugated to the Biovector present no inhibition of cellular proliferation. Under the same conditions, the lipofectamine presents significant toxicity, which on the one hand does not allow for increasing the concentration of ribozymes, and on the other hand makes it difficult to compare the activity of the active and inactive ribozymes.

Thus, the Biovector make it possible to increase considerably the biological activity of the ribozymes advantageously with respect to the prior art.

EXAMPLE 13

Specific Inhibition of the Synthesis of a Protein by an Antisense Conjugated to the Biovectors Biovector are prepared according to the protocol described in Example 4, whose NPSs have defined characteristics (for example, a charge of 1.6 mEq/g and a crosslinkage rate of 10%).

Two conjugates of oligonucleotide-Biovector are prepared from a phosphorothioate antisense targeting the mRNA of the prooncogene Erb2 (15 mers, Genset, France), and from the same phosphodiester antisense sequence (15 mers, Genset, France). At the same time, the control conjugates with a scrambled sequence conjugated to the Biovector and empty biovectors, were prepared. These different conjugates are prepared according to the protocol described in Example 6, with a ratio of oligonucleotide/NPS of 10%. By comparison, the same antisenses are conjugated to DOTAP.

In these experiments, $7 \times 1^4$ SK-Br3 cells (human adenocarcinoma line which superexpresses the protein P185-Erb2) in 300 µL RPMI 1640 (Gilco, France) are incubated in the presence of the various preparations: oligonucleotide and Biovector conjugate, free oligonucleotide, or free biovector. The incubations are carried out at a concentration of 180 µg/mL of biovector, corresponding to a concentration of 3 µM in oligonucleotide. After 5 h of incubation, 1 mL RPMI 1640 supplemented with 5% fetal calf serum is added to the cellular suspensions, and the cells are again incubated at 37° C.

After 72 h of incubation, the cells are tested for the presence of the protein P185-Erb2. For this test, the cells are collected, washed in PBS, and incubated in the presence of an anti-Erb-2 antibody (OP39, Oncogene Science, France). The cells are analyzed with a cytometer in flux after detection by a second antibody labeled with fluorescein.

The results obtained and presented in FIG. 8 show the contribution of the conjugation to the Biovector in the expression of the biological activity of an antisense. It is particularly noteworthy that there is no significant difference between the activity of the phosphodiester antisense and the phosphorothioate antisense. This lack of difference is certainly the expression of the protection of oligonucleotides after conjugation to the biovectors. On the other hand, the antisenses are twice as active after conjugation to the Biovector than after conjugation to the cationic lipids which are traditionally used (DOTAP).

EXAMPLE 14

In Vitro Biological Activity of an Antisense Conjugated to the Biovector Model Erb-2)

Oligonucleotide-Biovector conjugates are prepared under the conditions described in Example 13, and using the phosphorothioate derivative of this example.

For these proliferation experiments, $5 \times 10^3$ SK-Br cells in 60 µL RPMI 1640 (Gilco, France) are incubated in the presence of the various preparations, conjugate of oligonucleotide phosphorothioate and biovector, free oligonucleotide phosphorothioate or free biovector. The incubations are carried out at a concentration of 180 µg/mL of biovector, corresponding to a concentration of 3 µM in oligonucleotide. After 5 h of incubation, a quantity of 200 µL of RPMI 1640 supplemented with 5% fetal calf serum is added to the cellular suspensions, and the cells are again incubated at 37° C.

At different times, 24, 48, 72, 96, and 120 h, the cells are collected by trypsinization and counted on a cell counter (Coultronics, France). The results are the average of six experimental points.

FIG. 9 shows the proliferation curve of the cells after treatment with different preparations. Under these conditions, the free oligonucleotide is incapable of inhibiting cellular proliferation. It is noteworthy that the oligonucleotide targeting an oncogene makes it possible, after conjugation to the biovectots, to completely inhibit the cellular proliferation of this tumor line.

Bibliographic references
1) Uhlmann, E., & Peyman, A. (1990) Chem. Rev., 90, 543–583.
2) Wagner, R. W (1994) Nature, 372, 333–335.
3) Stein, C. A., & Cohen, J. S. (1988) Cancer Res., 48, 26S9–2668.
4) Helene, C., & Toulme, J. J. (1990) Biochim. Biophys. Acta, 1049, 99–125.
5) Thuong, N. T., & Helene, C. (1993) Angew. Chem. Int. Ed. Engl., 32, 666–690.
6) Pantopoulos, K., Johansson, H. E., & Hentze, M. W. (1994) Prog. Nucleic Acids Res. Mol. Biol., 48, 181–238.
7) Stein, C. A., & Cheng, Y.-C. (1993)Science, 261, 14004–1012.
8) Gura, T (1995) Science, 270, 575–577.
9) Woolf, T. D. (1995) Antisense Res. Dev., 5, 227–232.
10) Miller, P. S. (1996) Prog. Nucleic Acids Res. Mol. Biol., 52, 261–291.
11) Melton, D. A. (1985), Proc. Natl. Acad. Sci. USA, 82, 144–148.
12) Maher, J., & Dolnick, B. J. (1988) Nucleic Acids Res., 16, 3341–3358.
13) Liebhaber, S. A., Cash, F., Eshleman, S. S. (1992) J. Mol. Biol., 226, 609–621.
14) Johansson, H. E., Belsham, G. J., Sproat, B. S., & Hentze M. W. (1994) Nucleic Acids Res., 22,4591–4598.
15) Bonham, M. A., Brown, S., Boyd, A. L., Brown, P. H., Bruckenstein, D. A., Hanvey, J. C., Thomson, S. A., Pipe, A., Hassman, F., Bisi, J. E., Froehler, B. C., Matteucci, M. D., Wagner, R. W., Noble, S. A., & Babiss, L. E. (1995) Nucleic Acids Res, 23, 1197–1203.
16) Helene, C. and Toulme, J. J. (1990) Biochim. Biophys. Acta 1049, 99–125.
17) Stein C. A. and Cheng, Y. C. (1993) Science 261, 1004–1012.
18) Stein C. A. and Cheng, Y. C. (1988) Cancer Res. 48, 2659–68.
19) Simons M., Edelman, E. R., DeKeyser, J. L., Langer, R. and Rosenberg, R. D. (1992) Nature 359, 67–70.
20) Whitesell, L. Geselowitz, D., Chavany, C., Fahmi, B;, Walbridge, S., Alger, J. R. and Neckers, L. M. (1993) Proc. Natl. Acad. Sci. USA 90, 4665–4669.
21) Stein, C. A. and Krieg, A. M. (1994) Antisense Res. Dev. 4, 67–69.
22) Stein, C. A. (1995) Nature Medicine 1, 1119–1121.
23) Vlassov, V. V., Balakireva, L. A. and Yakubov, L. A. (1994) Biochim. Biophys. Acta 1197, 95–108.
24) Leonetti, J. P., Degols, G., Clarenc, J. P., Mechti, N. and Lebleu, B. (1993) Prog. Nucl. Acid. Res. Mol. Biol 44, 143–66.
25) Wagner, R. W. (1994) Nature 372, 333–335.
26) Uhlmann, E. and Peyman, A. (1990) Chem. Rev. 90, 544–584.
27) Clarenc, J. P., Degols, G., Leonetti, J. P., Milhaud, P. and Lebleu, B. (1993) Anticancer Drug Res. 8, 81–94.
28) Cazenave, C., Stein, C. A., Loreau, N., Thuong, N. T., Neckers, L. M., Subasinghe, C. Helene, C., Cohen, J. S. and Toulme, J. J. t1989) Nucleic Acids Res. 17, 4255–4273.
29) Iversen, P. L., Mata, J., Tracewell, W. G. and Zon, G. (1994) Antisense Res. Dev. 4, 43–52.
30) Srinivasan, S. K. and Iversen, P. (1995) J. Clin. Lab. Anal. 9, 129–137.
31) Bayever, E. and Iversen, P. (1995) J. Clin Lab. Anal. 9, 129–137.
32) Watson, P. H., Pon, R. T. and Shiu, R. P. (1992) Exp. Cell Res. 202, 391–7.

33) Storey, A., Oates, D., Banks, L., Crawford, L. and Crook, T. (1991) Nucleic Acids Res. 19, 4109–4114.
34) Thierry, A. R. and Dritschilo, A. (1992) Nucleic Acids Res. 20, 5691–8.
35) Zelphati, O., Imbach, J. L., Signoret, N., Zon, G., Rayner, B. and Lesemian, L. (1994) Nucleic Acids Res. 22,4307–4314.
36) Ropert, C., Lavignon, M., Dubernet, C., Couvreur, P. and Malvy, C. (1992) Biochem. Biophys. Res. Commun. 183, 879–885.
37) Leonetti, J. P., Machy, P.; Degols, G., Lebleu, B. and Leserman, L. (1990) Proc. Natl. Acad. Sci. USA 87, 2448–2451.
38) De Smidt, P., Le Doan, T., De Falco, S. and Van Berkel, T. (1991) Nucleic Acids Res. 19, 4695 700.
39) Krieg, A. M., Tonkinson, J., Matson, S., Zhao, Q., Saxon, M., Zhang, L. M., Bhanja, U., Yakubov, L. and Stein, C. A. (1993) Proc. Natl. Acad. Sci. USA 90, 1048–1052.
40) Dean, N. M. and McKay, R. (1994) Proc. Natl. Acad. Sci. USA 91, 11762–11766.
41) Capaccioli, S., Dipasquale, G., Mini, E., Mazzei, T. and Quattrone, A. (1993) Biochem. Biophys. Res. Commun. 197, 818–825.
42) Yeoman, L. C., Danels, Y. J. and Lynch, M. J. (1992) Antisense Res. Dev. 2, 51–59.
43) Saijo, Y., Perlaky, L., Wang, H. M. and Busch, H. (1994) Oncol. Res. 6, 243–249.
44) Chavany, C. Saison-Behmoaras, T., Ledoan, T., Puisieux, F., Couvreur, P. and Helene, C. (1994) Pharm. Res. 11, 1370–1378.
45) Schwab, G., Chavany, C., Duroux, I., Goubin, G., Lebeau, J., Helene, C. and Saison-Belinoaras, T. (1994) Proc. Natl. Acad. Sci. USA 91, 10460–10464.

What is claimed is:

1. An ionic conjugate, stable in a biological medium, of a particle vector comprising at least one non-liquid cationic hydrophilic nucleus, and polyanionic oligonucleotide, wherein said nucleus comprises a matrix of polysaccharides or oligosaccharides naturall or chemically crosslinked in an amount essentially equal to crosslinkage obtained between 10 and 15 mol % of epichlorhydrin per mole of ose in the polysaccharides or oliposaccharides.

2. A conjugate according to claim 1, wherein the particle vector comprises at least one nonliquid hydrophilic nucleus made up of a polysaccharide or oligosaccharide matrix, naturally or chemically crosslinked, and modified by cationic ligands, of which the positive charge rate is between 0.6 and 1.8 mEq of positive charges per gram of nucleus.

3. A conjugate according to claim 2, wherein the level of positive charges is between 0.8 and 1.6 mEq of positive charges per gram of nucleus.

4. A conjugate of a particle vector and oligonucleotides according to claim 1, wherein the particle vector includes at least one nonliquid hydrophilic nucleus made up of a polysaccharide or oligosaccharide matrix, naturally or chemically crosslinked, and modified by cationic ligands, of which the level of positive charge is between 0.6 and 1.8 mEq of positive charges per gram of nucleus, and the crosslinkage rate is essentially that obtained by crosslinkage between 10 and 15 mol % of epichlorhydrin per mole of ose in the polysaccharides or oligosaccharides, and wherein said particle vector is conjugated by ionic bonds which are stable in a biological medium to polyanionic oligonucleotides protected by said particle vector, wherein said polyanionic oligonucleotides hybridize with a cellular mRNA.

5. A conjugate according to claim 1, wherein the polysaccharides of the matrix are selected from the group consisting of dextran, starch, cellulose, their derivatives and substitutes, their hydrolysis products, and their salts and esters.

6. A conjugate according to claim 1, wherein the nonliquid hydrophilic nucleus is completely or partially covered by at least one layer of amphiphilic compounds.

7. A conjugate according to claim 6, wherein the amphiphilic compounds are selected from the group consisting of natural or synthetic lipids and phospholipids, ceramides, fatty acids, glycolipids, lipoproteins, and surfactants.

8. A conjugate according to claim 6, wherein the nonliquid hydrophilic nucleus is completely or partially covered by an external layer consisting essentially of natural or synthetic phospholipids or ceramides.

9. A conjugate according to claim 8, wherein said phospholipids or ceramides are associated with other amphiphilic compounds.

10. A conjugate according to claim 6, wherein the nonliquid hydrophilic nucleus is completely or partially covered by an external layer made up of natural fatty acids, fixed to the nucleus by covalent bonds.

11. A conjugate according to claim 1, wherein the nonliquid hydrophilic nucleus is completely or partially covered by two layers of arnphiphilic compounds.

12. A conjugate according to claim 11, wherein the nonliquid hydrophilic nucleus is completely or partially covered by a first layer of fatty acids, which is itself completely or partially covered by a lipid layer.

13. A conjugate according to claim 1, comprising an active principle combined with the nucleus or external layer, wherein said active principle is involve in the transport, addressing, or presentation of the conjugate to the cell membrane or in the cell's cytoplasm.

14. A conjugate according to claim 1, wherein the oligonucleotides are oligodeoxyribonucleotides or oligoribonucleotides, antisense or ribozymes.

15. A conjugate according to claim 14, wherein said oligonucleotides are labeled, natural or modified.

16. A particle vector comprising a conjugate according to claim 1.

17. A particle vector according to claim 16, wherein polysaccharides of the matrix are selected from the group consisting of dextran, starch, cellulose, their derivatives and substitutes, their products of hydrolysis, and their salts and esters.

18. A particle vector according to claim 16, wherein the nonliquid hydrophilic nucleus is completely or partially covered by at least one layer of amphiphilic compounds.

19. A particle vector according to claim 18, wherein the amphiphillic compounds are selected from the group consisting of natural or synthetic lipids and phospholipids, ceramides, fatty acids, glycolipids, lipoproteins, and surfactants.

20. A particle vector according to claim 19, wherein the nonliquid hydrophilic nucleus is completely or partially covered by a layer made up of natural fatty acids fixed to the nucleus by covalent bonds.

21. A particle vector according to claim 20, wherein the layer of fatty acids is itself completely or partially covered with a lipid layer.

22. A particle vector according to claim 18, wherein the nonliquid hydrophilic nucleus is completely or partially covered by an external layer consisting essentially of natural or synthetic phospholipids or ceramides.

23. A particle vector according to claim 22, wherein said phospholipids or ceramides are associated with other amphiphilic compounds.

24. A particle vector according to claim 16, wherein the polysaccharides or oligosaccharides, naturally or chemically linked, are modified by cationic ligands, of which the level of positive charges is between 0.6 and 1.8 mEqs per gram of nucleus.

25. A method for transfecting an oligonucleotide into a cell, the method comprising contacting said cell with a conjugate according to claim 1.

26. A process for the preparation of an ionic conjugate which is stable in a biological medium, of a particle vector comprising at least one nonliquid cationic hydrophilic nucleus and short sequences of polyanionic nucleic acid, said process comprising the following stages:

a) preparation of the cationic nucleus
by mixing a hydrophilic polymer which is polysaccharide or oligosaccharide in nature, chemically or naturally crosslinked with a crosslinkage agent in a ratio of between 0.06 and 0.2 mole, of crosslinkage agent per unit of ose in the polysaccharide or oligosaccharide
and adding a cationic ligand to the above mixture to obtain a level of charge of the nucleus between 0.6 and 1.8 per gram of nucleus;

b) the charging of the polyanionic oligonucleotides
by adding to the nucleus prepared in stage (a), under agitation, between about 0.02 and 0.4 g of oligonucleotide per grain of nucleus, at a rate of about 0.25 µg of oligonucleotide per mg of nucleus and per hour, and 6 mg per mg of nucleus and per hour at a temperature between about 20° C. and 60° C.

27. A process according to claim 26, wherein prior to stage (b), a layer made up of amphiphilic compounds is grafted to all or part of the nucleus prepared in stage (a).

28. A process according to claim 27, wherein a second layer made up of amphiphilic compounds is grafted to all or part of the first layer covering the nucleus.

29. A process according to claim 26, wherein stage (b) consists of adding to particle vectors prepared according to stage (a), with or without external layer(s) of amphiphilic compound, whose concentration, expressed in cationic nucleus, is between 1 and 20 mg/mL, a solution of oligonucleotides at a concentration between 1 and 20 mg/mL, to obtain a ratio of oligonucleotide/particle vectors between 2 and 40% inclusive, according to an addition kinetics of the oligonucleotide solution between 5: L/mL/h and 300: L/mL/h, and at an incubation temperature between 20° C. and 60° C.

30. A process according to claim 26 wherein said crosslinkage agent is present in a ratio of between 0.1 and 0.15 mole of crosslinkage agent per unit of ose in the polysaccharide or oligosaccharide,
wherein the level of charge is between 0.8 and 1.6 in meqs per gram of nucleus,
wherein the amount of oligonucleotide per gram of nucleus is between 0.05 and 0.2 g,
wherein the oligonucleotide is added at a rate of between 4 µg/mg/h and 1 mg/mg/h, and,
wherein the temperature is between 40° and 50° C.

* * * * *

UNITED STATES PATENT AND TRADEMARK OFFICE
CERTIFICATE OF CORRECTION

PATENT NO. : 6,214,621 B1
DATED : April 10, 2001
INVENTOR(S) : Betbeder et al.

It is certified that error appears in the above-identified patent and that said Letters Patent is hereby corrected as shown below:

Column 19,
Line 39, now reads "or oligosacchrides naturall or chemically" should read -- or oligosacchrides naturally or chemically --;
Line 42, now reads "polysacchrides or oliposacchrides" should read -- polysacchrides or oligosacchrides --;

Column 22,
Line 22, now reads "0.8 and 1.6 in meqs per gram" should read -- 0.8 and 1.6 in mEqs per gram --.

Signed and Sealed this

Eighth Day of January, 2002

*Attest:*

*Attesting Officer*

JAMES E. ROGAN
*Director of the United States Patent and Trademark Office*